United States Patent [19]

Karasawa et al.

[11] Patent Number: 5,276,185
[45] Date of Patent: Jan. 4, 1994

[54] PROCESS FOR PRODUCING AMIDE COMPOUNDS

[75] Inventors: Minato Karasawa; Masamitsu Inomata; Hiroharu Kageyama; Masahiro Tokumitsu; Sinji Tokunoh; Kanemitsu Miyama, all of Chiba, Japan

[73] Assignee: Mitsui Toatsu Chemicals, Inc., Tokyo, Japan

[21] Appl. No.: 997,111

[22] Filed: Dec. 24, 1992

Related U.S. Application Data

[63] Continuation of Ser. No. 712,907, Jun. 7, 1991, abandoned.

[30] Foreign Application Priority Data

Jun. 11, 1990 [JP] Japan ................... 2-149960

[51] Int. Cl.$^5$ ............................ C07C 231/06
[52] U.S. Cl. .................................... 564/126
[58] Field of Search .................. 564/126, 124, 130

[56] References Cited

U.S. PATENT DOCUMENTS

| | | | |
|---|---|---|---|
| 3,366,639 | 1/1968 | Haefele | 260/295 |
| 3,699,164 | 10/1972 | Fine et al. | 564/126 |
| 3,794,682 | 2/1974 | Barber | 260/561 N |
| 4,018,829 | 4/1977 | Gruber et al. | 260/561 B |
| 4,950,801 | 8/1990 | Ebata et al. | 564/126 |
| 4,987,256 | 1/1991 | Ebata et al. | 564/126 |

FOREIGN PATENT DOCUMENTS

| | | |
|---|---|---|
| 0418512 | 3/1991 | European Pat. Off. . |
| 2131813 | 3/1972 | Fed. Rep. of Germany . |
| 2103663 | 4/1972 | France . |
| 63-57534 | 3/1988 | Japan . |
| 63-57535 | 3/1988 | Japan . |

OTHER PUBLICATIONS

Derwent Wpil Online Abstract, 88-108793, Derwent Publications Ltd., London, GB JP-A-63-057 535, Abstract. 1988.
Derwent Wpil Online Abstract, 88-108792, Derwent Publications Ltd., London, GB JP-A-63-057 534, Abstract. 1988.

*Primary Examiner*—Glennon H. Hollrah
*Assistant Examiner*—Brian M. Burn
*Attorney, Agent, or Firm*—Burns, Doane, Swecker & Mathis

[57] ABSTRACT

Amides are produced by reacting nitriles with water in a liquid phase in the presence of a manganese oxide containing an element selected from Groups IIIA, IVA, VA, IIIB, IVB, VB, VIB and VIII of the Periodic Table.

13 Claims, No Drawings

PROCESS FOR PRODUCING AMIDE COMPOUNDS

This application is a continuation of application Ser. No. 07/712,907, filed Jun. 7, 1991, now abandoned.

BACKGROUND OF THE INVENTION

1. Field of the Invention

The present invention relates to a process for producing amide compounds by reacting nitrile compounds with water in a liquid phase.

2. Description of the Related Art

Amide compounds are very useful as intermediates for organic syntheses which can be starting materials for agricultural chemicals, pharmaceuticals, synthetic resins and the like. In particular, methyl methacrylate can be produced by a vapor phase reaction of α-hydroxyisobutyramide (hereinafter referred to as "HAM") in the presence of methyl alcohol and a solid acid catalyst (Japanese Patent Application Publication Nos. 10,940/1988 and 63,537/1988).

It is known that amide compounds can be produced by the reaction of the corresponding nitrile compounds with water and further, various catalysts useful for this reaction are also known. U.S. Pat. No. 3,366,639 discloses a manganese oxide which is one of such catalysts. Copper-containing catalysts often used for the hydration reaction of nitrile compounds can give only an insufficient effect in hydration of α-hydroxynitrile compounds such as acetone cyanohydrin (hereinafter referred to as "ACH") and the like. On the contrary, manganese oxides give fairly good results in hydration of α-hydroxynitrile compounds as shown in West German Patent No. 2,131,813. However, as is clear from the description in Japanese Patent Application Laid-open No. 222/1977, a particular skill is necessary for preparing the manganese oxides active in hydration of nitrile compounds disclosed in West German Patent No. 2,131,813, and moreover, there is a problem that the characteristics of the catalyst produced are different from batch to batch.

SUMMARY OF THE INVENTION

An object of the present invention is to provide a process for producing amides by hydration of nitriles efficiently in the presence of a manganese oxide catalyst.

Another object of the present invention is to provide a manganese oxide catalyst substantially free from fluctuation in catalytic characteristics in the hydration of nitriles.

A further object of the present invention is to provide a manganese oxide catalyst having an improved catalytic activity in the hydration of nitriles.

Still another object of the present invention is to provide a manganese oxide catalyst having a long catalyst life which is important as an industrial catalyst.

According to the present invention, there is provided a process for producing an amide compound which comprises reacting a nitrile compound with water in a liquid phase in the presence of a catalyst essentially consisting of manganese oxide containing an element selected from the group consisting of Groups IIIA, IVA, VA, IIIB, IVB, VB, VIB and VIII of the Periodic Table.

DESCRIPTION OF THE PREFERRED EMBODIMENTS

Exemplary suitable nitrile compounds which can be used in the present invention include compounds of the formula, $$R\text{-}CN$$

where R is selected from alkyl, cycloalkyl, alkenyl, cycloalkenyl, aryl, alkaryl, aralkyl and heterocyclic groups each of which may be unsubstituted or substituted with halogen, alkoxy, nitro, ester, ketone, or hydroxy. Further, polynitriles may be also used.

The manganese oxide used in the present invention may be anhydrous or hydrated. As the manganese oxide, manganese dioxide produced by known methods may be used. The known production methods are, for example, a method of reducing a permanganate at 20–100° C. at a neutral or an alkaline region (Zeit. Anorg. Allg. Chem., 309. pp. 1–32 and pp. 121–150 (1961)), a method of treating potassium permanganate and manganese sulfate in an acidic condition (J. Chem. Soc.,1953, p. 2189 (1953)). A method of reducing a permanganate with a hydrohalic acid (Japanese Patent Application Laid-open No. 57,535/1988) and a method of electrolytic oxidation of an aqueous solution of manganese sulfate. In particular, manganese dioxide produced by the reaction of potassium permanganate or sodium permanganate with manganese sulfate under acidic conditions is preferred.

Examples of elements of Groups IIIA, IVA, VA, IIIB, IVB, VB, VIB and VIII include boron, aluminum, gallium, indium, and thallium; carbon, silicon, germanium, tin, and lead; nitrogen, phosphorus, arsenic, antimony, and bismuth; scandium, yttrium, lanthanum, cerium, praseodymium, neodymium, samarium, and thorium; titanium, zirconium, and hafnium; vanadium, niobium, and tantalum; chromium, molybdenum, and tungsten; and iron, ruthenium, osmium, cobalt, rhodium, iridium, nickel, palladium, and platinum.

One or more of these elements are incorporated in manganese dioxide.

Among them, manganese dioxide containing at least one element of Groups IIIA, IVA, VA, IIIB, and VIII of the Periodic Table is preferable.

Aluminum is preferable in Group IIIA, tin and lead in Group IVA, antimony and bismuth in Group VA, scandium and lanthanum in Group IIIB, and iron, cobalt and nickel in Group VIII.

The elements to be incorporated in the manganese dioxide catalyst are usually used in the form of nitrate, chloride, sulfate, carbonate, phosphate, hydroxide, oxide, simple substance or the like.

The amount of the element contained in manganese dioxide is usually 0.005–0.50 atom, preferably 0.01–0.2 atom per one atom of the total manganese.

Salts, hydroxides, oxides, simple substance or the like of elements of Groups IIIA, IVA, VA, IIIB, IVB, VB, VIB and VIII of the Periodic Table may be incorporated in manganese dioxide by conventional methods usually used in the preparation of catalysts, for example, impregnation, kneading or coprecipitation. In particular, the following methods are preferable, e.g. a method comprising impregnating manganese dioxide with a salt of the element and neutralizing with an alkali or the like, and a method comprising effecting the reaction of sodium permanganate or potassium permanganate with manganese sulfate in the presence of a salt of the element and, after completion of the reaction, neutralizing the catalyst solution with ammonia or the like.

The catalyst solution is filtered and the filter cake is washed with water and then dried at 80°-200° C. in air. The resulting catalyst is shaped into the desired form suitable for a hydration reaction in which said catalyst is to be used. It is particularly preferable to incorporate the element in the form of hydroxide and/or oxide in manganese dioxide according to the above-mentioned preparation method.

The amount of the catalyst used in the present invention is usually 0.01-0.50 part by weight per one part of the starting material, i.e. the nitrile compound, in the case of batch system. The concentration of the catalyst in a reaction vessel is usually 1% by weight or more, preferably 2-30% by weight in the case of a continuous reaction system of a fluidized catalyst bed type.

The amount of water used for the hydration reaction of the nitrile compound in the present invention is usually one mole or more, preferably 5-30 moles per one mole of the nitrile group of the nitrile compound.

As a reaction solvent, water is usually used, but when the nitrile compound is hydrophobic, a solvent capable of enhancing the compatibility with water is used which may be, for example, lower alcohols such as methyl alcohol, ethyl alcohol and the like, ethers such as 1,4-dioxane, tetrahydrofuran and the like, ketones such as acetone and the like, dimethyl-sulfoxide, N,N-dimethylformamide, N,N-dimethylacetamide, N-methyl-pyrrolidone and the like.

In particular, when a ketone cyanohydrin is used as the nitrile compound, it is desirable to use usually 0.1-3.0 moles of the ketone constituting the nitrile compound per one mole of the nitrile compound in addition to the above-mentioned reaction solvent in order to suppress the decomposition of the ketone cyanohydrin. For example, when an α-hydroxynitrile compound such as ACH is used, it is desirable to add acetone as shown in Japanese Patent Application Laid-open No. 222/1977.

The reaction temperature is usually 0°-200° C., preferably 10°-150° C., more preferably 30°-80° C.

The reaction pressure is not critical as long as the pressure is sufficient to keep the reactants in a liquid state at the reaction temperature. That is, reduced pressure, atmospheric pressure or high pressure may be used provided that the above conditions are satisfied.

The process of the present invention is carried out in a liquid phase and may be effected batchwise or continuously. In the case of a continuous system, there may be used a fluidized catalyst bed or a fixed catalyst bed. When a reactor of a fluidized catalyst bed type is used, the reactor outlet is provided with a metal or glass filter or the like so that the ground catalyst particles may not flow out.

The liquid raw materials, i.e. nitrile compound, water and reaction solvent, may be fed to the reactor in the form of a mixture thereof or separately.

The residence time of the reaction fluid in the reactor may be appropriately set so as to convert a nitrile compound to the corresponding amide compound in high conversion and high selectivity.

The amide product solution obtained in high yield flowing out from the reactor is subjected to distillation to distill away the solvent and the resulting product is crystallized and separated in water, ether and/or acetone solvents to recover the end product, the amide compound.

According to the present invention, hydration of nitriles can be efficiently carried out in the presence of a manganese oxide catalyst to produce amides.

The manganese oxide catalyst containing the specified element exhibits catalytic characteristcs which are substantially free from fluctuation, and have high catalytic activity and/or a very long catalyst life which is an important factor when used in an industrial process.

The present invention will be explained further in detail referring to the following examples and comparison The "%" in the following is molar percent unless otherwise specified.

(1) Preparation of manganese dioxide catalysts containing the second element and activity test of the catalysts 1) Preparation of manganese dioxide To one liter of an aqueous solution of manganese (II) sulfate (395 g/liter) was added sulfuric acid to prepare an aqueous solution of manganese (II) sulfate of pH 1. To the resulting aqueous solution was added 278.6 g of potassium permanganate to oxidize the manganese (II) sulfate and one liter of water was added to the resulting slurry and aged for 30 min. while keeping the temperature at about 50° C. The product thus aged was subjected to vacuum filtration by an aspirator and then washed with one liter of 7% (by weight) aqueous ammonia and 3 liters of water to obtain manganese dioxide.

2) Preparation of manganese dioxide catalysts containing the second element (Impregnation or kneading)

Catalyst $A_1$ 2.45 g of ferric nitrate nonahydrate was dissolved in 100 g of distilled water and to the resulting aqueous solution, 10 g of manganese dioxide (atomic ratio of Fe/Mn=0.053) prepared as above was added and the pH of the resulting solution was adjusted to 7 with 28% (by weight) aqueous ammonia. Then the aqueous solution was concentrated to dryness. The resulting solid matter was dried at 120° C. for 5 hours, and then calcined at 400° C for 4 hours to obtain Catalyst $A_1$.

Catalyst B

Using cobalt nitrate hexahydrate 1.67 g (atomic ratio of Co/Mn=0.050), prepared in the same manner as Catalyst $A_1$.

Catalyst C

Using nickel nitrate hexahydrate 3.35 g (atomic ratio of Ni/Mn=0.100), prepared in the same manner as Catalyst $A_1$.

Catalyst D

Using sodium nitrate 0.05 g (atomic ratio of Na/Mn=0.005), prepared in the same manner as Catalyst $A_1$.

Catalyst E

Using anhydrous barium chloride 0.48 g (atomic ratio of Ba/Mn=0.020), prepared in the same manner as Catalyst $A_1$.

Catalyst F

Using anhydrous aluminum chloride 3.07 g (atomic ratio of Al/Mn=0.200), prepared in the same manner as Catalyst $A_1$.

Catalyst G

Using tin tetrachloride 1.50 g (atomic ratio of Sn/Mn=0.050), prepared in the same manner as Catalyst $A_1$.

Catalyst H

Prepared by sufficiently kneading 0.41 g of graphite with 10 g of manganese dioxide prepared as above (atomic ratio of C/Mn=0.300) followed by drying at 120° C. for 9 hours.

Catalyst I

Using scandium nitrate tetrahydrate 0.35 g (atomic ratio of Sc/Mn=0.010), prepared in the same manner as Catalyst $A_1$.

Catalyst J

Using lanthanum nitrate hexahydrate 2.62 g (atomic ratio of La/Mn=0.053), prepared in the same manner as Catalyst $A_1$.

Catalyst K

Using titanium tetrachloride 2.19 g (atomic ratio of Ti/Mn=0.100), prepared in the same manner as Catalyst $A_1$.

Catalyst L

Using zirconiun oxychloride octahydrate 1.95 g (atomic ratio of Zr/Mn=0.053), Prepared in the same manner as Catalyst $A_1$.

Catalyst M

Using vanadium oxytrichloride 1.00 g (atomic ratio of V/Mn=0.050), prepared in the same manner as Catalyst $A_1$.

Catalyst N

Using chromium nitrate nonahydrate 4.60 g (atomic ratio of Cr/Mn=0.100), prepared in the same manner as Catalyst $A_1$.

Catalyst P

Using bismuth nitrate pentahydrate 5.58 g (atomic ratio of Bi/Mn=0.100), prepared in the same manner as Catalyst $A_1$.

Catalyst $A_2$:

The procedure for the preparation of Catalyst $A_1$ was repeated except that ferric nitrate nonahydrate was not added, Catalyst $A_2$ was obtained.

3) Activity test of catalyst

COMPARISON EXAMPLE 1

In a 100 ml round bottom flask equipped with a reflux condenser and a thermometer were placed the above-mentioned Catalyst $A_2$ 4.8 g, ACH 16.0 g, acetone 16.5 g, and water 16.9 g, and a reaction was carried out with stirring at 40° C. for 3 hours. In the liquid raw material mixture, the molar ratio of ACH:acetone:water was 1:1.5:5 and the pH was 2.8.

The catalyst was filtered off from the reaction fluid and then the catalyst was washed with water. A mixture of the filtrate and the rinsing water was analyzed by gas chromatography The conversion of ACH was 33.4% and the selectivity of HAM was 85.7%.

COMPARISON EXAMPLE 2

The procedure of Comparison Example 1 was repeated by using the same catalyst $A_2$. The result is shown in Table 1. As is clear from Table 1, there is fluctuation in the catalyst characteristics between Comparison Examples 1 and 2 where the same Catalyst $A_2$ was used and the catalytic activity is poor.

EXAMPLES 1-15

The procedure of Comparison Example 1 was repeated except that Catalyst $A_2$ was replaced with one of Catalyst $A_1$ and Catalyst B to Catalyst P as mentioned above.

The results shown in Table 1 below indicate that the catalytic characteristics of the manganese oxide catalyst containing an element selected from Groups IIIA, IVA, VA, IIIB, IVB, VB, VIB, and VIII of the Periodic Table are markedly improved as compared with those of the manganese oxide catalyst devoid of such element.

Therefore, it will be noted that the present invention is very useful for hydration of nitrile compounds such as ACH and the like.

(2) Life test of manganese dioxide catalyst containing the second element

1) Preparation of manganese dioxide catalyst containing the second element (coprecipitation method) To one liter of an aqueous solution of manganese (II)sulfate (395 g/liter) was added sulfuric acid to prepare an aqueous solution of manganese (II) sulfate of pH 1.

To the resulting solution was added a salt of the respective element such that the respective element was present in an amount of 0.02-0.20 atom per one atom of the total manganese (Mn(II)+Mn(VII)). To the resulting solution was added 278.6 g of potassium permanganate to oxidize the manganese compound, and then one liter of water was added to the resulting slurry, which was then aged for 30 min. while keeping the temperature at about 50° C. To the solution thus aged was added 28% (by weight) aqueous ammonia to adjust the pH of the solution to 7 followed by stirring for one hour. The resulting solution was vacuum filtered using an aspirator, and the filter cake was washed with 3 liter of water and dried at 120° C. for 12 hours to obtain a manganese dioxide catalyst containing the second element.

Further, the above-mentioned procedure was repeated except that the salt of the second element was not added, and a manganese dioxide catalyst void of the second element was prepared.

2) Life test of catalyst in the continuous hydration reaction of ACH

COMPARISON EXAMPLES 3-5 AND EXAMPLES 16-28

A pressure resistant reactor (inner volume 50 ml; equipped with a glass stirrer, a mercury thermometer, a raw material feeding opening, and a liquid outlet provided with a glass-ball-filter) was charged with 30 g of manganese dioxide catalyst of 60-100 mesh and 300 g of water and the inner temperature was kept at 60° C.

Then, a liquid raw material mixture (molar ratio of ACH:acetone:water being 1:1.5:18) was fed to the reactor at a flow rate of 37 ml/hr by a quantitative pump and the continuous hydration reaction was carried out for 20 days. The amount of liquid in the reactor was in the range of 290-310 ml.

As manganese dioxide catalysts, the manganese dioxide catalysts containing the second element and the manganese dioxide catalyst void of the second element prepared as mentioned above were used respectively.

The results are shown in Table 2.

TABLE 1

Test of Activity of Manganese Dioxide Catalyst containing Second Element

| | Added Element | Atomic Ratio of Added Element to Manganese | ACH Conversion (%) | HAM Selectivity (%) |
| --- | --- | --- | --- | --- |
| Comparison Example 1 | None | 0 | 33.4 | 85.7 |
| Comparison Example 2 | None | 0 | 18.2 | 80.7 |
| Example 1 | Fe | 0.053 | 93.1 | 96.8 |
| Example 2 | Co | 0.050 | 92.6 | 96.8 |
| Example 3 | Ni | 0.100 | 91.4 | 95.7 |
| Example 4 | Na | 0.005 | 89.8 | 94.9 |
| Example 5 | Ba | 0.020 | 92.5 | 96.1 |
| Example 6 | Al | 0.200 | 94.1 | 96.0 |

TABLE 1-continued

Test of Activity of Manganese Dioxide Catalyst containing Second Element

| | Added Element | Atomic Ratio of Added Element to Manganese | ACH Conversion (%) | HAM Selectivity (%) |
|---|---|---|---|---|
| Example 7 | Sn | 0.050 | 90.7 | 95.3 |
| Example 8 | C | 0.300 | 93.3 | 95.8 |
| Example 9 | Sc | 0.010 | 87.3 | 95.3 |
| Example 10 | La | 0.053 | 87.2 | 94.6 |
| Example 11 | Ti | 0.100 | 92.0 | 95.7 |
| Example 12 | Zr | 0.053 | 90.9 | 95.2 |
| Example 13 | V | 0.050 | 87.5 | 94.0 |
| Example 14 | Cr | 0.100 | 87.0 | 93.8 |
| Example 15 | Bi | 0.100 | 95.6 | 99.0 |

TABLE 2

Life Test of Manganese Dioxide containing Second Element

| | Salt of Added Element | Atomic Ratio of Added Element to Manganese | HAM Yield (%) | | | |
|---|---|---|---|---|---|---|
| | | | After 1 day | After 7 days | After 12 days | After 20 days |
| Comparison Example 3 | None | 0 | 84 | 83 | 29 | 7 |
| Example 16 | Fe(NO$_3$)$_2$ | 0.10 | 93 | 92 | 90 | 92 |
| Example 17 | Co(NO$_3$)$_2$ | 0.10 | 92 | 92 | 91 | 92 |
| Example 18 | Ni(NO$_3$)$_2$ | 0.10 | 91 | 90 | 90 | 90 |
| Comparison Example 4 | Na$_2$SO$_4$ | 0.10 | 89 | 89 | 60 | 19 |
| Comparison Example 5 | Ca(NO$_3$)$_2$ | 0.10 | 90 | 90 | 48 | 22 |
| Example 19 | Al(NO$_3$)$_3$ | 0.20 | 93 | 92 | 75 | 61 |
| Example 20 | SnCl$_2$ | 0.10 | 91 | 91 | 79 | 66 |
| Example 21 | Pb(NO$_3$)$_2$ | 0.10 | 93 | 93 | 90 | 89 |
| Example 22 | Sc(NO$_3$)$_3$ | 0.02 | 90 | 90 | 88 | 66 |
| Example 23 | La(NO$_3$)$_3$ | 0.02 | 91 | 91 | 87 | 70 |
| Example 24 | ZrOCl$_2$ | 0.05 | 90 | 90 | 87 | 49 |
| Example 25 | NH$_4$VO$_3$ | 0.05 | 87 | 87 | 80 | 38 |
| Example 26 | Cr(NO$_3$)$_3$ | 0.10 | 88 | 88 | 76 | 51 |
| Example 27 | SbCl$_3$ | 0.10 | 92 | 92 | 91 | 91 |
| Example 28 | Bi(NO$_3$)$_3$ | 0.10 | 89 | 89 | 88 | 86 |

What is claimed is:

1. A process for producing an α-hydroxycarboxylic acid amide comprising reacting an α-hydroxynitrile compound with water in a liquid phase in the presence of a catalyst consisting essentially of manganese dioxide containing an element selected from the group consisting of Groups IIIA, VA, IIIB, VIB, VIII of the Periodic Table and lead so as to obtain the corresponding α-hydroxycarboxylic acid amide said catalyst having an extended catalyst life compared to a catalyst containing an alkali metal or alkaline earth metal.

2. The process according to claim 1 in which the nitrile compound is acetone cyanohydrin.

3. The process according to claim 1 in which the catalyst is manganese dioxide containing an element of Group IIIA of the Periodic Table.

4. The process according to claim 1 in which the catalyst is manganese dioxide containing an element of Group VA of the Periodic Table.

5. The process according to claim 1 in which the catalyst is manganese dioxide containing an element of Group IIIB of the Periodic Table.

6. The process according to claim 1 in which the catalyst is manganese dioxide containing an element of Group VIII of the Periodic Table.

7. The process according to claim 1 in which the catalyst is manganese dioxide containing lead.

8. The process according to claim 1 in which the catalyst is manganese dioxide containing antimony.

9. The process according to claim 1 in which the catalyst is manganese dioxide containing bismuth.

10. The process according to claim 1 in which the catalyst is manganese dioxide containing iron.

11. The process according to claim 1 in which the catalyst is manganese dioxide containing cobalt.

12. The process according to claim 1 in which the catalyst is manganese dioxide containing nickel.

13. The process of claim 1 wherein the element contained in the manganese dioxide catalyst is present in an amount of 0.005-0.50 atom per one atom of the manganese.

* * * * *